US012605529B2

(12) United States Patent
Sakata et al.

(10) Patent No.: US 12,605,529 B2
(45) Date of Patent: Apr. 21, 2026

(54) APPLICATION CONTAINER

(71) Applicant: Sato Pharmaceutical Co., Ltd., Tokyo (JP)

(72) Inventors: Kota Sakata, Tokyo (JP); Kiyohiko Rikiishi, Tokyo (JP); Yoshinori Itoh, Tokyo (JP); Yoshitoshi Koyama, Tokyo (JP)

(73) Assignee: Sato Pharmaceutical Co., Ltd., Tokyo (JP)

( * ) Notice: Subject to any disclaimer, the term of this patent is extended or adjusted under 35 U.S.C. 154(b) by 409 days.

(21) Appl. No.: 18/559,843

(22) PCT Filed: Jul. 11, 2022

(86) PCT No.: PCT/IB2022/056371
§ 371 (c)(1),
(2) Date: Nov. 9, 2023

(87) PCT Pub. No.: WO2022/238984
PCT Pub. Date: Nov. 17, 2022

(65) Prior Publication Data
US 2024/0269444 A1 Aug. 15, 2024

(30) Foreign Application Priority Data

May 13, 2021 (JP) ................................. 2021-081699

(51) Int. Cl.
*A61M 35/00* (2006.01)
(52) U.S. Cl.
CPC .................................. *A61M 35/00* (2013.01)
(58) Field of Classification Search
CPC ..... A61M 35/00; A61M 35/003; B65D 83/00; A45D 34/04
See application file for complete search history.

(56) References Cited

U.S. PATENT DOCUMENTS 11,299,329 B2 * 4/2022 Sakata ................... B65D 47/42
2012/0187157 A1 7/2012 Yuan

FOREIGN PATENT DOCUMENTS

CN     112399810 A     2/2021
JP       04041979 Y     10/1992
(Continued)

OTHER PUBLICATIONS

PCT Office, International Search Report issued in PCT/IB2022/056371 dated Aug. 23, 2022.
(Continued)

*Primary Examiner* — Leslie R Deak
(74) *Attorney, Agent, or Firm* — Wood Herron & Evans LLP

(57) ABSTRACT

An application container (1) of the present invention includes: an inner plug member (20) mounted on a mouth portion (10) of a container main body (2) and formed with a communication hole (21) and a discharge hole (22); a holder (30) that includes an accommodating portion (31) and a plug body (35) and is formed with a communication path (40) between the holder (30) and the inner plug member (20); an application member (50) disposed in the accommodating portion (31); a biasing member (60) configured to bias the holder (30) upward with respect to the inner plug member (20); an overcap (4) mounted on the mouth portion (10) of the container main body (2); and a seal portion (80) configured to block communication between the communication path (40) and an outside, in a state where the overcap (4) is removed from the mouth portion (10) and the plug body (35) closes the communication hole (21).

4 Claims, 5 Drawing Sheets

(56)          References Cited

FOREIGN PATENT DOCUMENTS

| | | |
|----|----------------|---------|
| JP | H06002784 Y    | 1/1994  |
| JP | 2017095117 A   | 6/2017  |
| JP | 2018034859 A   | 3/2018  |
| JP | 2019077477 A   | 5/2019  |
| JP | 2019131232 A   | 8/2019  |
| JP | 2019209997 A   | 12/2019 |
| TW | 200714525 A    | 4/2007  |

OTHER PUBLICATIONS

New Zealand Intellectual Property Office, Office Action issued in NZ 805734 dated Jun. 16, 2025.
Russian Patent Office, Notice of Allowance issued in RU 2023130689 dated May 29, 2024.
Taiwan Patent Office, Office Action issued in TW 111126029 dated Sep. 18, 2025.

* cited by examiner

APPLICATION CONTAINER

TECHNICAL FIELD

The present invention relates to an application container. Priority is claimed on Japanese Patent Application No. 2021-081699, filed on May 13, 2021, the content of which is incorporated herein by reference.

BACKGROUND ART

In the related art, there has been known an application container that applies a content liquid such as a drug solution to a site to be applied such as the scalp or skin of the human body. For example, as shown in Patent Document 1 below, an application container of this type includes: an inner plug member that has a cylindrical shape, is mounted on a mouth portion of a container main body, and is formed with a communication hole which communicates with the inside of the container main body and a discharge hole which communicates with the communication hole and discharges the content liquid; an application member disposed inside the inner plug member to be movable toward a communication hole side in a state where a tip portion of the application member protrudes outside from the discharge hole; and a biasing member that biases the application member toward a discharge hole side. In the application container, a valve seat with which a valve body formed in the application member detachably comes into contact from the communication hole side is formed in a portion of the inner plug member between the communication hole and the discharge hole.

CITATION LIST

Patent Document

[Patent Document 1]
   Japanese Unexamined Patent Application, First Publication No. 2018-34859

SUMMARY OF INVENTION

Technical Problem

However, in the application container of the related art, since the communication between the communication hole and the discharge hole is blocked by the valve body and the valve seat when the application container is not used, it is necessary to remove the overcap and then push the application member to open the valve in order to allow the application member to impregnate the content liquid. Therefore, it is difficult to additionally impregnate the content liquid in the application member before use. Further, when the communication hole and the discharge hole are in constant communication, there is a possibility of the content liquid leaking from the discharge hole during use.

The present invention has been made in view of such circumstances, and an object of the present invention is to provide an application container capable of impregnating an application member with a content liquid before use while suppressing the leakage of the content liquid during use.

Solution to Problem

A first aspect of the present invention is an application container. The application container includes: an inner plug member having a cylindrical shape extending in a vertical direction, mounted on a mouth portion of a container main body, and formed with a communication hole which communicates with an inside of the container main body and a discharge hole which communicates with the communication hole and discharges a content liquid of the container main body; a holder including an accommodating portion that has a bottomed cylindrical shape and is supported movably along the vertical direction inside the inner plug member, and a plug body that opens the communication hole to be closable from below the communication hole in the container main body, and formed with a communication path between the holder and the inner plug member to communicate with an inside of the accommodating portion and an inside of the container main body; an application member disposed in the accommodating portion and protruding upward from the holder; a biasing member configured to bias the holder upward with respect to the inner plug member; an overcap mounted on the mouth portion of the container main body and configured to close the discharge hole in a state where a rise of the holder is regulated; and a seal portion configured to block communication between the communication path, which passes between an inner peripheral surface of the inner plug member and an outer peripheral surface of the accommodating portion, and an outside, in a state where the overcap is removed from the mouth portion and the plug body closes the communication hole.

According to the first aspect of the present invention, the inside of the accommodating portion and the inside of the container main body are in communication through the communication path in a state where the overcap is mounted on the mouth portion of the container main body, since the plug body opens the communication hole of the inner plug member. For this reason, by inverting or shaking the application container while the overcap is still mounted, the content liquid in the container main body can be supplied into the accommodating portion. At this time, since the discharge hole of the inner plug member is closed by the overcap, the application member can be impregnated with the content liquid before use while suppressing the leakage of the content liquid.

Furthermore, when the overcap is removed from the mouth portion of the container main body, the restriction on the rise of the holder is released, so that the plug body rises and closes the communication hole. This blocks the communication between the inside of the accommodating portion and the inside of the container main body, thereby preventing the leakage of the content liquid during use. Moreover, at this time, the seal portion blocks the communication between the communication path, which passes between the outer peripheral surface of the accommodating portion and the inner peripheral surface of the inner plug member, and the outside. Therefore, for example, it is possible to suppress the content liquid remaining in the communication path from leaking out from between the outer peripheral surface of the accommodating portion and the inner peripheral surface of the inner plug member.

As described above, it is possible to provide an application container capable of impregnating an application member with a content liquid before use while suppressing the leakage of the content liquid during use.

In a second aspect of the application container of the present invention, the seal portion includes: a first seal protrusion portion provided on the inner peripheral surface of the inner plug member; and a second seal protrusion portion provided on the outer peripheral surface of the accommodating portion and positioned below the first seal protrusion portion, and a space between the inner peripheral surface of the inner plug member and the outer peripheral surface of the accommodating portion is sealed by the first seal protrusion portion and the second seal protrusion portion coming into contact with each other, in a state where the overcap is removed from the mouth portion and the plug body closes the communication hole.

According to the second aspect of the present invention, the space between the inner peripheral surface of the inner plug member and the outer peripheral surface of the accommodating portion is sealed by the first seal protrusion portion and the second seal protrusion portion that come into contact with each other, in a state where the overcap is removed from the mouth portion and the plug body closes the communication hole. In this manner, the space between the inner peripheral surface of the inner plug member and the outer peripheral surface of the accommodating portion can be reliably sealed by the seal portion.

Moreover, in a state where the overcap is mounted on the mouth portion, in a case where the first seal protrusion portion and the second seal protrusion portion are not in contact with each other, and the first seal protrusion portion and the second seal protrusion portion come into contact with each other during the holder rising with respect to the inner plug member after the overcap is removed from the mouth portion, it becomes possible to suppress the sliding resistance between the holder and the inner plug member to a low level, enabling smooth vertical movement of the holder with respect to the inner plug member.

In a third aspect of the application container of the present invention, the container further includes: a first regulating protrusion portion provided on the inner peripheral surface of the inner plug member; and a second regulating protrusion portion provided on the outer peripheral surface of the accommodating portion. In the application container, the first regulating protrusion portion and the second regulating protrusion portion are configured to come into contact with each other in the vertical direction, in a state where the overcap is removed from the mouth portion and the plug body closes the communication hole, and the seal portion blocks communication between the communication path and the outside.

According to the third aspect of the present invention, when the inner plug member or the holder changes with time, there is a possibility that the plug body excessively bites into the inner plug member due to the biasing force of the biasing member. Such a time-dependent change may occur, for example, when a state where the overcap is removed from the mouth portion of the container main body or a state where the intermediate product (application plug), in which the inner plug member and the holder are combined, is not used as a component of the application container, is maintained for a long period of time.

Here, in a state where the overcap is removed from the mouth portion, the plug body closes the communication hole, and the seal portion blocks communication between the communication path and the outside, the first regulating protrusion portion and the second regulating protrusion portion come into contact with each other in the vertical direction. Therefore, as described above, even when the plug body tends to excessively bite into the inner plug member due to the biasing force of the biasing member, the first regulating protrusion portion and the second regulating protrusion portion are locked, so that a rise of the holder can be regulated. As a result, excessive biting of the plug body into the inner plug member is regulated.

Advantageous Effects of Invention

According to the present invention, it is possible to provide an application container capable of impregnating an application member with a content liquid before use while suppressing the leakage of the content liquid during use.

DESCRIPTION OF EMBODIMENTS

Hereinafter, an embodiment of an application container according to the present invention will be described with reference to FIGS. 1 to 5.

Figure 1:
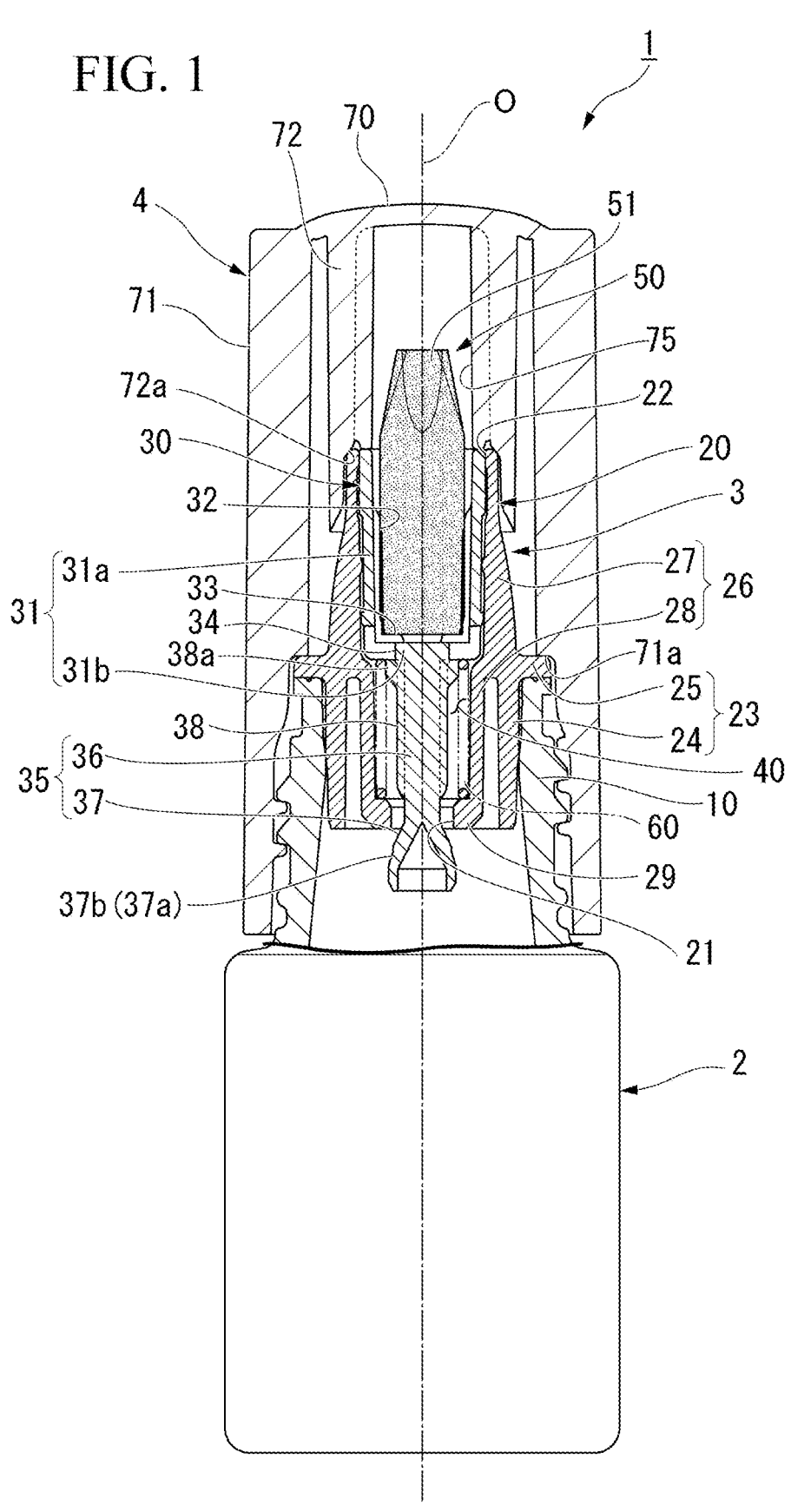
FIG. 1 is a cross-sectional view showing an application container of an embodiment.
Figure 2:
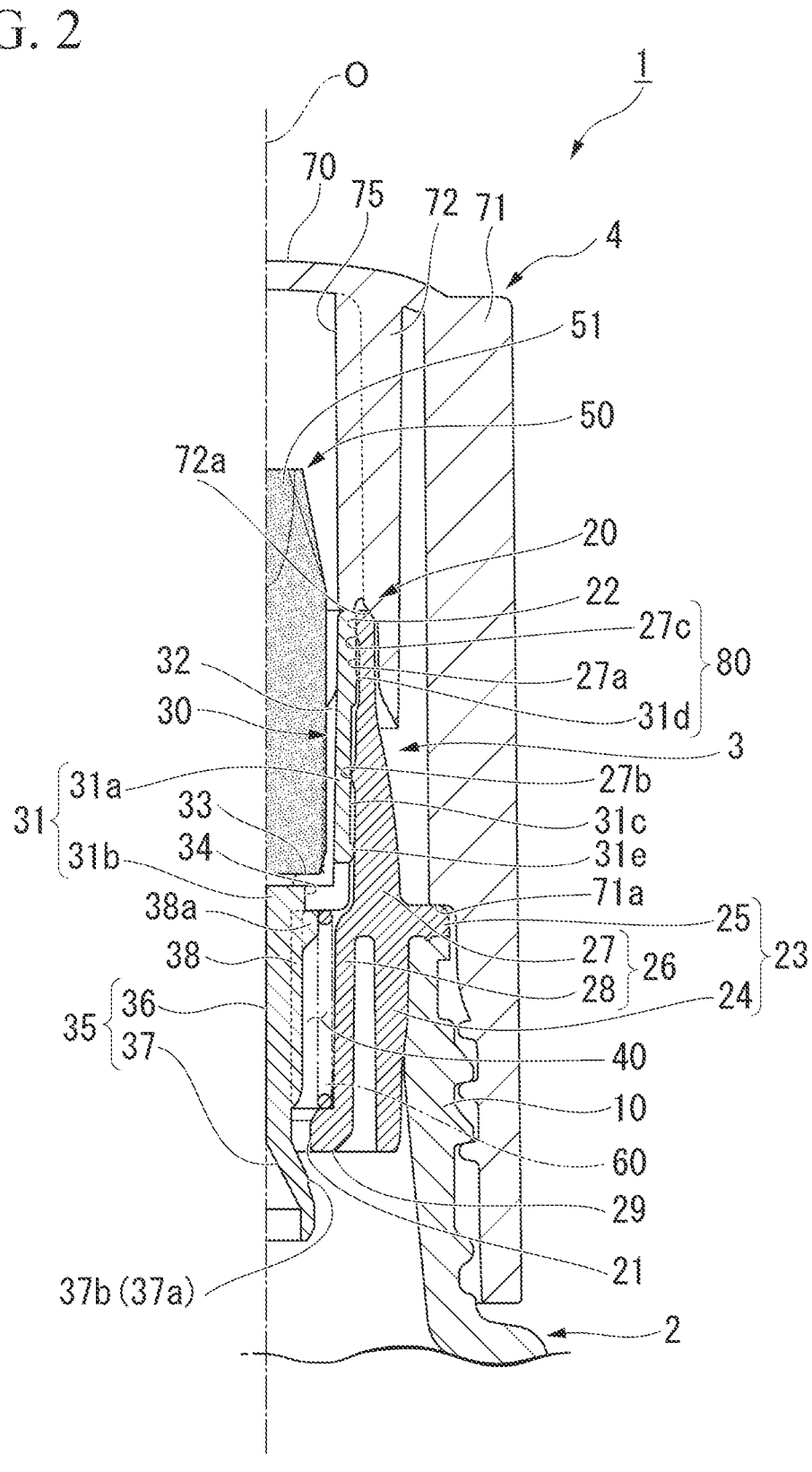
FIG. 2 is an enlarged cross-sectional view of a main part in the cross-sectional view shown in FIG. 1.
Figure 3:
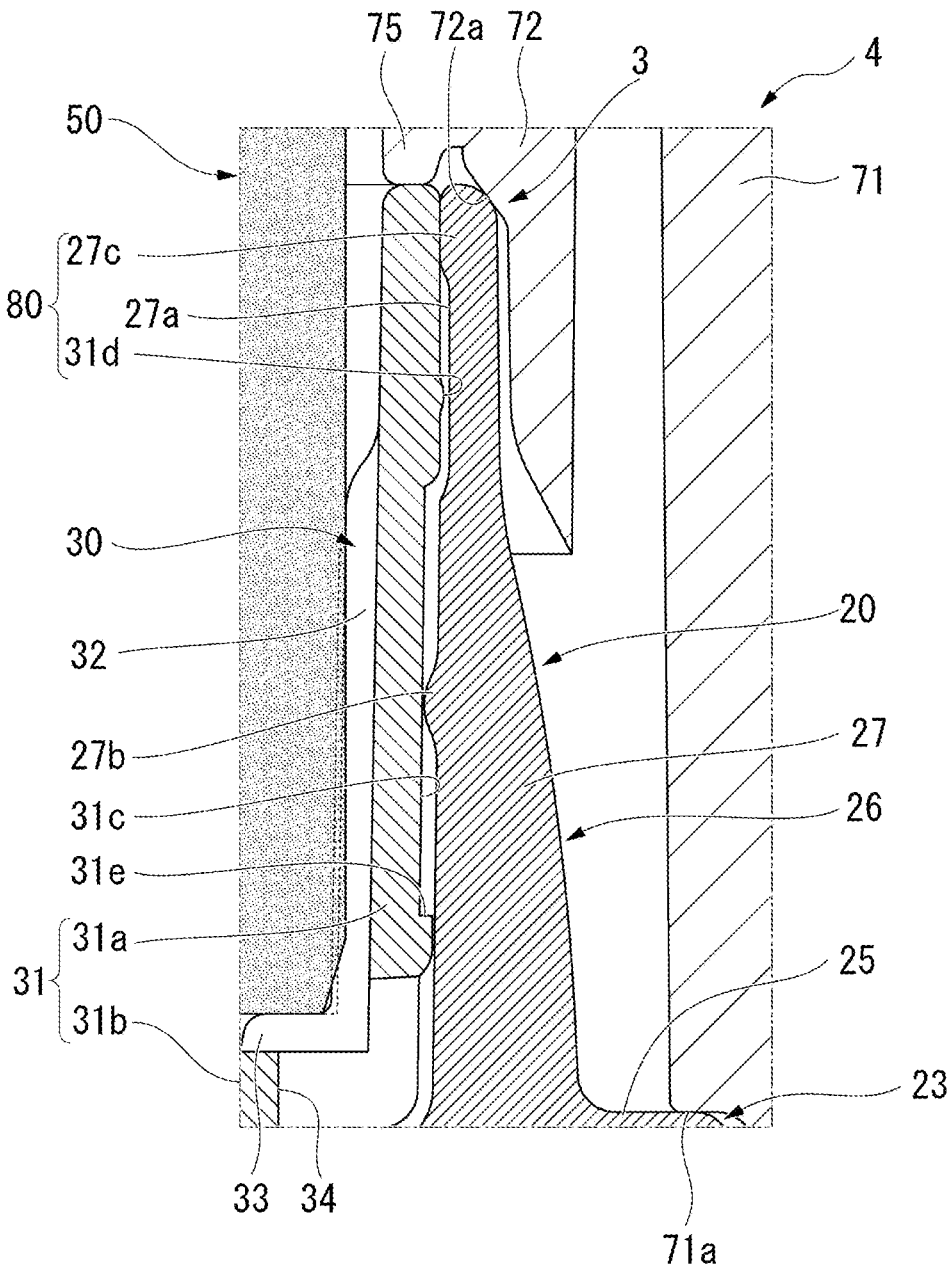
FIG. 3 is an enlarged cross-sectional view of a main part in the cross-sectional view shown in FIG. 2.

As shown in FIGS. 1 to 3, an application container 1 according to the present embodiment includes a container main body 2 that has a bottomed cylindrical shape and accommodates a content liquid to be applied to a site to be applied, an application plug 3 that has a cylindrical shape and is mounted inside a mouth portion 10 of the container main body 2, and an overcap 4 that has a topped cylindrical shape and is removably mounted on the mouth portion 10 of the container main body 2 to cover the application plug 3. Incidentally, the content liquid is not particularly limited, and examples of the content liquid include liquid such as medicines or cosmetics which are to be applied to a site to be applied such as the human body or the skin.

The central axes of the container main body 2, the application plug 3, and the overcap 4 are disposed on a common axis. In the present embodiment, the common axis is referred to as a container axis O, a direction along the container axis O is referred to as a vertical direction, and an overcap 4 side along the vertical direction is referred to as 'upward' and a side opposite the overcap 4 side (container main body 2 side) along the vertical direction is referred to as 'downward'. The overcap 4 side along the vertical direction may be referred to as an upper side, a direction toward a side opposite the overcap 4 side (container main body 2 side) may be referred to as a lower side, and a direction toward the overcap 4 side along the vertical direction may be referred to as upward and a direction toward a side opposite the overcap 4 side (container main body 2 side) may be referred to as downward. In addition, in a plan view seen in the container axis O, a direction intersecting the container axis O is referred to as a radial direction and a direction rotating around the container axis O is referred to as a circumferential direction.

The mouth portion 10 of the container main body 2 has a smaller diameter than portions (shoulder portion, body portion, and bottom portion) of the container main body 2 other than the mouth portion 10. In the shown example, a male screw is formed on an outer peripheral surface of the mouth portion 10 of the container main body 2.

The application plug 3 includes an inner plug member 20 having a cylindrical shape, mounted on the mouth portion 10 of the container main body 2, and formed with the communication hole 21 that opens downward to communicate with the inside of the container main body 2, and the discharge hole 22 that communicates with the communication hole 21 and opens upward to discharge the content liquid, a holder 30 disposed inside the inner plug member 20, an application member 50 held by the holder 30 and protruding upward from the holder 30, and a biasing member 60 that biases the holder 30 upward with respect to the inner plug member 20.

The inner plug member 20 includes a mounting cylinder portion 23 mounted on the mouth portion 10 of the container main body 2 and a discharge cylinder portion 26 in which a communication hole 21 and a discharge hole 22 are formed. The mounting cylinder portion 23 includes a fitting portion 24 which is formed in a cylindrical shape and is tightly fitted inside the mouth portion 10 of the container main body 2 and a flange portion 25 that has an annular shape and extends radially outward from an upper end portion of the fitting portion 24, and is disposed on the upper end opening edge of the mouth portion 10. As a result, the mounting cylinder portion 23 is mounted on the mouth portion 10 in a state of being inserted into the mouth portion 10.

The discharge cylinder portion 26 is connected to the mounting cylinder portion 23 and extends both upward and downward from the mounting cylinder portion 23. An upper end opening of the discharge cylinder portion 26 is the discharge hole 22. A lower end opening of the discharge cylinder portion 26 is the communication hole 21. The discharge cylinder portion 26 is connected to the mounting cylinder portion 23 at an intermediate portion in the vertical direction. The discharge cylinder portion 26 includes a protruding cylinder 27 extending upward from the upper end portion of the fitting portion 24 of the mounting cylinder portion 23 and a hanging cylinder 28 extending downward inside the mounting cylinder portion 23 from the lower end portion of the protruding cylinder 27.

The outer diameter of the protruding cylinder 27 is smaller than the outer diameter of the flange portion 25 of the mounting cylinder portion 23. As shown in FIGS. 2 and 3, the inner peripheral surface of the protruding cylinder 27 is provided with a first recessed portion 27a and a first regulating protrusion portion 27b.

The first recessed portion 27a is disposed above the center of the protruding cylinder 27 in the vertical direction. The first recessed portion 27a has an annular shape and extends over the entire circumference in the circumferential direction. The size (width) of the first recessed portion 27a in the vertical direction is larger than the size (depth) of the first recessed portion 27a in the radial direction. In the protruding cylinder 27, the portion positioned above the first recessed portion 27a is a first seal protrusion portion 27c.

The first seal protrusion portion 27c is disposed at an upper end portion of the protruding cylinder 27. The first seal protrusion portion 27c has an annular shape and extends over the entire circumference in the circumferential direction. The size of the first seal protrusion portion 27c in the vertical direction is smaller than the size of the first recessed portion 27a in the vertical direction. In a longitudinal cross-sectional view along the vertical direction, the surface of the first seal protrusion portion 27c has a linear shape extending in the vertical direction. The first seal protrusion portion 27c extends over the entire vertical direction with a constant inner diameter. The inside of the first seal protrusion portion 27c (inside the upper end portion of the protruding cylinder 27) is the discharge hole 22.

The first regulating protrusion portion 27b is disposed below the first recessed portion 27a. The first regulating protrusion portion 27b has an annular shape and extends over the entire circumference in the circumferential direction. In a longitudinal cross-sectional view along the vertical direction, the surface of the first regulating protrusion portion 27b has a semicircular shape that protrudes radially inward.

As shown in FIG. 1, the hanging cylinder 28 is disposed with a gap in the radial direction with respect to the fitting portion 24. A lower end portion of the hanging cylinder 28 is positioned at the same position as the lower end portion of the fitting portion 24 in the vertical direction. However, the position of the lower end portion of the hanging cylinder 28 is not particularly limited. The hanging cylinder 28 is formed such that the inner diameter thereof is smaller than the inner diameter of the protruding cylinder 27. The inner peripheral surface of the hanging cylinder 28 extends with a constant inner diameter except for the lower end portion. That is, the inner peripheral surface of the hanging cylinder 28 extends with a constant inner diameter in the portion of the hanging cylinder 28 other than the lower end portion. A pedestal portion 29 that has an annular shape and protrudes radially inward is formed in a lower end portion of the hanging cylinder 28. The communication hole 21 is formed in a lower end portion of the pedestal portion 29.

The holder 30 includes an accommodating portion 31 that has a bottomed cylindrical shape, and is supported movably along the vertical direction inside the inner plug member 20, and a plug body 35 that opens the communication hole 21 to be closable from below the communication hole 21. The accommodating portion 31 is disposed coaxially with the container axis O. The accommodating portion 31 has a peripheral wall 31a and a bottom wall 31b, and is surrounded by the protruding cylinder 27 of the discharge cylinder portion 26. An upper end portion of the peripheral wall 31a is disposed at a position equal to the upper end portion of the protruding cylinder 27 in the vertical direction. The upper end portion of the peripheral wall 31a can protrude further upward from the protruding cylinder 27.

A fitting rib 32 that protrudes radially inward and extends in the vertical direction is formed on the inner peripheral surface of the peripheral wall 31a. A plurality of the fitting ribs 32 are formed at intervals in the circumferential direction. The outer diameter of the bottom wall 31b is larger than the inner diameter in the upper portion of the hanging cylinder 28. A pedestal protrusion portion 33 protruding upward is formed on an upper surface of the bottom wall 31b. A plurality of the pedestal protrusion portions 33 are formed at intervals in the circumferential direction at an outer peripheral portion of the upper surface of the bottom wall 31b. The circumferential position of the pedestal protrusion portion 33 is equal to the circumferential position of the fitting rib 32. A radially outer end portion of the pedestal protrusion portion 33 is continuous with a lower end portion of the fitting rib 32.

A flow hole 34 is formed in the accommodating portion 31. The flow hole 34 is formed across the peripheral wall 31a and the bottom wall 31b. A plurality of the flow holes 34 are formed at intervals in the circumferential direction. Accordingly, the inside of the accommodating portion 31 and the outside of the accommodating portion 31 are in communication through the flow holes 34. However, a place where the flow hole 34 is formed is not limited to the position described above. For example, the place of the flow hole 34 may be formed to penetrate the bottom wall 31*b* in the vertical direction, or may be formed to penetrate the peripheral wall 31*a* in the radial direction.

As shown in FIGS. 2 and 3, the outer peripheral surface of the accommodating portion 31 is provided with a second recessed portion 31*c*, a second regulating protrusion portion 31*e*, and a second seal protrusion portion 31*d*.

The second recessed portion 31*c* has an annular shape and extends over the entire circumference in the circumferential direction. The size of the second recessed portion 31*c* in the vertical direction is equal to or larger than half the size of the accommodating portion 31 in the vertical direction. The distance from an upper end edge of the second recessed portion 31*c* to an upper end edge of the accommodating portion 31 is longer than the distance from a lower end edge of the second recessed portion 31*c* to a lower end edge of the accommodating portion 31. The lower end edge of the second recessed portion 31*c* is positioned above an upper end edge of the flow hole 34. The size (width) of the second recessed portion 31*c* in the vertical direction is larger than the size (depth) of the second recessed portion 31*c* in the radial direction. In the second recessed portion 31*c*, the first regulating protrusion portion 27*b* is disposed to be movable in the vertical direction.

In the accommodating portion 31, the second regulating protrusion portion 31*e* is provided above the flow hole 34 and below the second recessed portion 31*c*. The second regulating protrusion portion 31*e* is provided adjacent to the flow hole 34 in the vertical direction. The second regulating protrusion portion 31*e* (upper surface of the second regulating protrusion portion 31*e*) constitutes the side surface of the second recessed portion 31*c*. The second regulating protrusion portion 31*e* has an annular shape, and extends over the entire circumference in the circumferential direction. The second regulating protrusion portion 31*e* (upper surface of the second regulating protrusion portion 31*e*) faces the first regulating protrusion portion 27*b* from below. The upper surface of the second regulating protrusion portion 31*e* is a flat surface extending in the radial direction. The lower surface of the second regulating protrusion portion 31*e* is a curved surface that extends radially inward as it goes downward. Due to such a shape of the lower surface of the second regulating protrusion portion 31*e*, in a case where the holder 30 is combined with the inner plug member 20 from above, the second regulating protrusion portion 31*e* easily transitions smoothly over the first regulating protrusion portion 27*b* in the vertical direction.

The second seal protrusion portion 31*d* is disposed above the second recessed portion 31*c*. The second seal protrusion portion 31*d* has an annular shape and extends over the entire circumference in the circumferential direction. In a longitudinal cross-sectional view along the vertical direction, the surface of the second seal protrusion portion 31*d* has a semicircular shape that protrudes radially inward. The second seal protrusion portion 31*d* is disposed to be movable in the first recessed portion 27*a* in the vertical direction. The outer diameter of the second seal protrusion portion 31*d* is larger than the inner diameter of the first seal protrusion portion 27*c*.

As shown in FIG. 1, the plug body 35 extends from the inside of the discharge cylinder portion 26, passing through the communication hole 21, and extending downward below the discharge cylinder portion 26. The plug body 35 includes a shaft portion 36 extending downward from the bottom wall 31*b* of the accommodating portion 31 and a plug main body 37 supported by a lower end portion of the shaft portion 36. The shaft portion 36 extends in the vertical direction centering around the container axis O. The shaft portion 36 is formed such that the entire of a portion facing the discharge cylinder portion 26 in the radial direction is spaced at intervals in the radial direction from the inner peripheral surface of the discharge cylinder portion 26. The lower end portion of the shaft portion 36 is positioned inside the hanging cylinder 28. However, the lower end portion of the shaft portion 36 may protrude downward from the communication hole 21 of the hanging cylinder 28. A longitudinal rib 38 which protrudes radially outward and extends in the vertical direction is formed on an outer peripheral surface of the shaft portion 36. A plurality of the longitudinal ribs 38 are formed at intervals in the circumferential direction. Upper end portions of the longitudinal ribs 38 are connected to lower surfaces of the bottom wall 31*b* of the accommodating portion 31. The longitudinal ribs 38 extend radially at intervals from the inner peripheral surface of the discharge cylinder portion 26. A protruding portion 38*a* protruding radially outward is formed at the upper end portion of the longitudinal rib 38. The radially outer end edge of the protruding portion 38*a* is positioned radially inward from the inner surface of the hanging cylinder 28 and overlaps with the flow hole 34 in the radial direction.

The plug main body 37 forms a lower portion of the plug body 35. The plug main body 37 is formed in a shape of a rotating body centered around the container axis O and has an inverted V-shaped longitudinal cross-sectional shape. A lower end portion of the plug main body 37 is positioned below the lower end portion of the hanging cylinder 28, and the lower end portion of the plug main body 37 is formed such that the outer diameter thereof is larger than the inner diameter of the communication hole 21. The plug main body 37 includes an outer peripheral surface 37*a* that is contiguous with an outer peripheral surface of the shaft portion 36 and extends in the circumferential direction. The outer peripheral surface 37*a* of the plug main body 37 is formed in a substantially conical surface shape as a whole so that the lower end edge is positioned radially outward from the upper end edge. A first sealing surface 37*b*, which is brought into close contact with the inner peripheral surface or the lower end surface (lower end edge) of the communication hole 21, is formed in a portion of the outer peripheral surface 37*a* in the vertical direction.

The plug body 35 is formed such that the entire of a portion facing the discharge cylinder portion 26 in the radial direction is spaced at intervals in the radial direction from the inner peripheral surface of the discharge cylinder portion 26. In this manner, the communication path 40 that communicates the inside of the accommodating portion 31 and the inside of the container main body 2 with the flow hole 34 and the communication hole 21 as both ends is formed between the holder 30 and the discharge cylinder portion 26. Then, the plug main body 37 rises with respect to the discharge cylinder portion 26, so that the first sealing surface 37*b* comes into close contact with the inner peripheral surface or the lower end surface (lower end edge) of the communication hole 21, and thus the plug main body 37 closes the communication hole 21 from below, and then communication between the inside of the accommodating portion 31 and the inside of the container main body 2 through the communication path 40 is blocked.

The application member 50 is formed in a columnar shape coaxial with the container axis O. The application member 50 is disposed in the accommodating portion 31 to protrude further upward from the accommodating portion 31. The application member 50 is placed on the pedestal protrusion portions 33. The application member 50 protrudes upward from the discharge hole 22. In the shown example, the upper end portion of the application member 50 is formed in a shape with a ridge portion disposed at the uppermost part by being processed such that the cut surfaces 51 face each other in the radial direction. However, the shape of the upper end portion of the application member 50 is not limited to the shown example, and may be appropriately changed according to a site to be applied. The application member 50 is formed of an impregnation material capable of being impregnated with the content liquid. Examples of the impregnation material include a porous material such as a sponge, a fibrous body in which synthetic fibers are solidified by a resin solution and which can be impregnated with the content liquid by the capillary phenomenon, and the like.

The biasing member 60 is a coil spring centered around the container axis O. The biasing member 60 is disposed in a compressed state between the hanging cylinder 28 of the inner plug member 20 and the holder 30. An upper end portion of the biasing member 60 is externally fitted into the protruding portion 38a of the longitudinal rib 38 in a state of being in contact with the bottom wall 31b of the accommodating portion 31 of the holder 30 from below the bottom wall 31b. The lower end portion of the biasing member 60 is supported by the pedestal portion 29 of the hanging cylinder 28 of the inner plug member 20 from below the biasing member 60.

The overcap 4 includes a top wall portion 70 formed in a circular shape in a top view, an outer cylinder portion 71 extending downward from an outer peripheral edge of the top wall portion 70, and an inner cylinder portion 72 extending downward from the top wall portion 70 and disposed inside the outer cylinder portion 71.

The lower end portion of the outer cylinder portion 71 is disposed to surround the mouth portion 10 of the container main body 2. The lower end portion of the outer cylinder portion 71 has a female screw on the inner peripheral surface thereof and is screwed into the mouth portion 10. The inner diameter of the lower end portion of the outer cylinder portion 71 is larger than the inner diameter of a remaining portion (portion positioned above the lower end portion) of the outer cylinder portion 71. The inner peripheral surface of the lower end portion of the outer cylinder portion 71 and the inner peripheral surface of the remaining portion are contiguous with each other through an annular stepped surface 71a. The stepped surface 71a is in contact with the flange portion 25 of the mounting cylinder portion 23 of the inner plug member 20 from above the flange portion 25.

The lower end portion of the inner cylinder portion 72 is disposed to surround the upper end portion of the protruding cylinder 27. The inner diameter of the lower end portion of the inner cylinder portion 72 is larger than the inner diameter of the remaining portion (portion positioned above the lower end portion) of the inner cylinder portion 72. The remaining portion of the inner cylinder portion 72 is disposed to surround the portion of the application member 50 that protrudes upward from the discharge cylinder portion 26. The inner peripheral surface of the lower end portion of the inner cylinder portion 72 and the inner peripheral surface of the remaining portion are contiguous with each other through a second sealing surface 72a, which is an annular stepped surface. The second sealing surface 72a extends upward and radially inward from the lower end portion of the inner cylinder portion 72 toward the remaining portion. The second sealing surface 72a is an inclined surface. The second sealing surface 72a is in close contact with the upper end edge of the discharge cylinder portion 26 over the entire circumference. Accordingly, the inner cylinder portion 72 and the top wall portion 70 close the discharge hole 22. Specifically, an outer edge of the upper end edge of the discharge cylinder portion 26 is in contact with the second sealing surface 72a. In addition, in the present embodiment, the outer edge of the upper end edge of the discharge cylinder portion 26 is a curved surface.

Regulating ribs 75 which protrude radially inward and extend in the vertical direction are formed on the inner peripheral surface of the inner cylinder portion 72. The regulating ribs 75 are provided in the remaining portion of the inner cylinder portion 72. An upper end edge of the regulating rib 75 is contiguous with the top wall portion 70. A plurality of the regulating ribs 75 are formed at intervals in the circumferential direction. The regulating rib 75 is formed to be spaced apart from the application member 50. A lower end edge of the regulating rib 75 is spaced apart from the discharge cylinder portion 26. A portion of the lower end edge of the regulating rib 75 protrudes downward and is in contact with the upper end edge of the accommodating portion 31 of the holder 30 from above the accommodating portion 31. In this manner, the overcap 4 regulates the rise of the holder 30, which is in an upwardly biased state by the biasing member 60.

Next, an operation of the above-described application container 1 will be described.

As shown in FIGS. 1 to 3, in a state where the overcap 4 is mounted on the mouth portion 10 of the container main body 2 (hereinafter, also referred to as an initial state), since the plug body 35 of the holder 30 opens the communication hole 21 of the inner plug member 20, the inside of the accommodating portion 31 and the inside of the container main body 2 are in communication through the communication path 40. For this reason, by inverting or shaking the application container 1 while the overcap 4 is still mounted, the content liquid in the container main body 2 can be supplied into the accommodating portion 31. Since the discharge hole 22 of the inner plug member 20 is closed by the inner cylinder portion 72 of the overcap 4, the application member 50 can be impregnated with the content liquid before use while suppressing the leakage of the content liquid.

In this case, the communication path 40 and the outside of the application plug 3 (inside of the inner cylinder portion 72) are in communication through the space between the inner peripheral surface of the protruding cylinder 27 and the outer peripheral surface of the accommodating portion 31 (through the discharge hole 22). That is, the communication path 40 and the outside of the application plug 3 (inside of the inner cylinder portion 72) are in communication through the space (discharge hall 22) between the inner peripheral surface of the protruding cylinder 27 and the outer peripheral surface of the accommodating portion 31.

Figure 4:
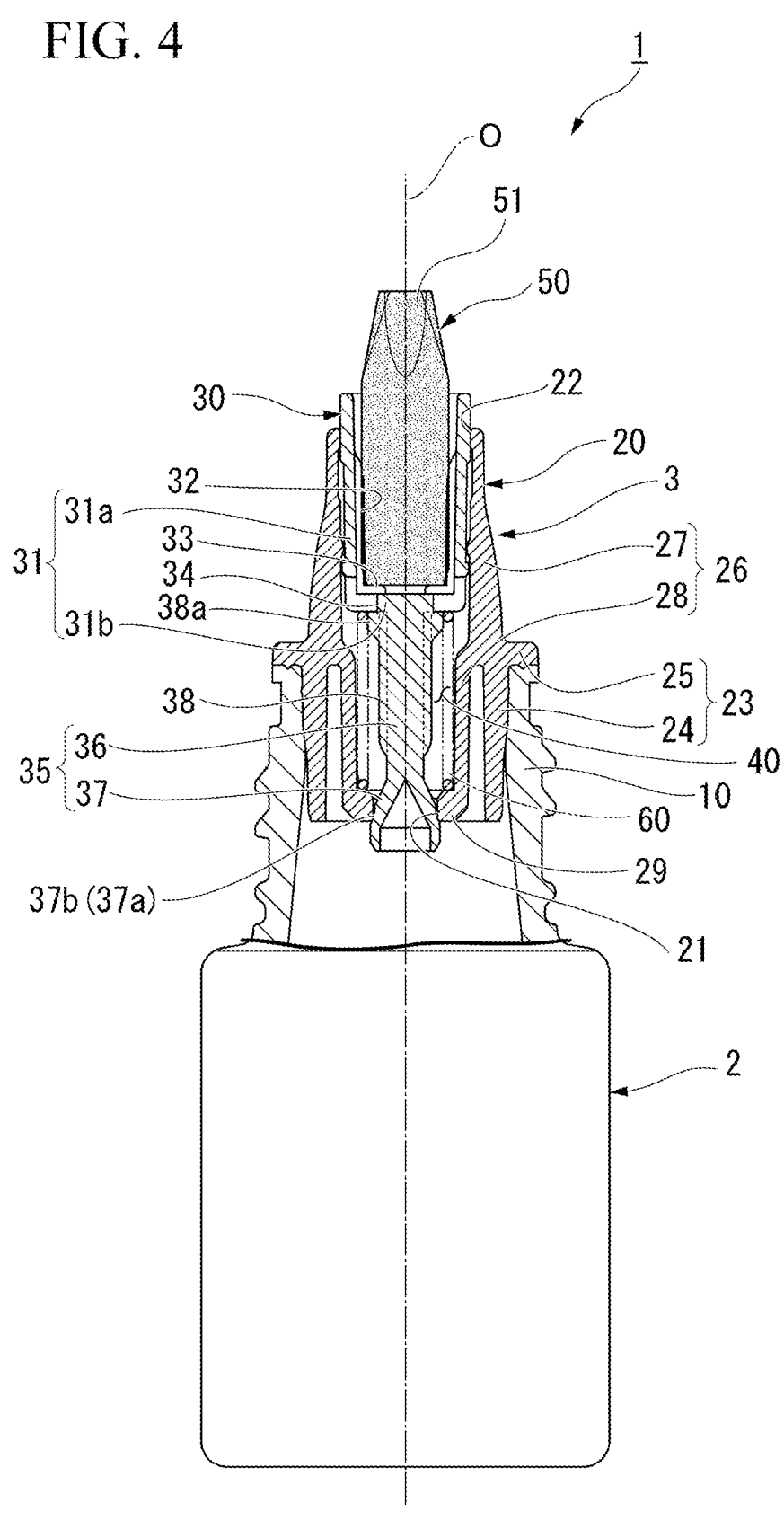
FIG. 4 is a cross-sectional view of the application container in a state where an overcap is removed from the application container in the state shown in FIG. 1.
Figure 5:
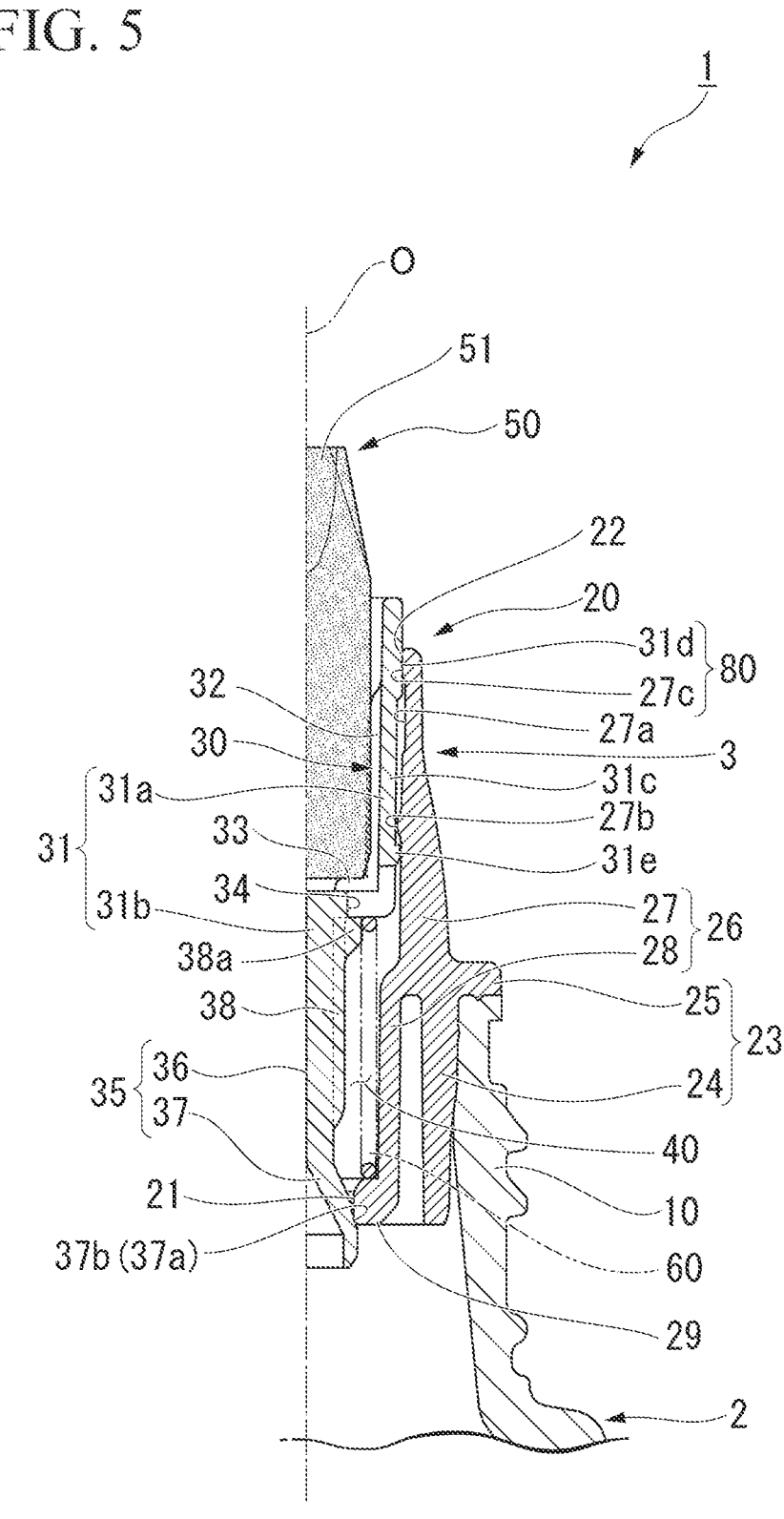
FIG. 5 is an enlarged cross-sectional view of a main part in the cross-sectional view shown in FIG. 4.

Furthermore, as shown in FIGS. 4 and 5, when the overcap 4 is removed from the mouth portion 10 of the container main body 2, the regulation on the rise of the holder 30 by the regulating rib 75 is released. Accordingly, the plug body 35 rises to close the communication hole 21. This blocks the communication between the inside of the accommodating portion 31 and the inside of the container main body 2, thereby suppressing the leakage of the content liquid during use. Moreover, at this time, the space between the inner peripheral surface of the inner plug member 20 and the outer peripheral surface of the accommodating portion 31 is sealed by the first seal protrusion portion 27c and the second seal protrusion portion 31d coming into contact with each other. That is, the second seal protrusion portion 31d, which was positioned in the first recessed portion 27a in the initial state, comes upward out of the first recessed portion 27a and is positioned radially inward with respect to the first seal protrusion portion 27c. In this case, for example, the surface of the first seal protrusion portion 27c and the surface of the second seal protrusion portion 31d are brought into pressure contact with each other, and the space between the inner peripheral surface of the inner plug member 20 and the outer peripheral surface of the accommodating portion 31 is sealed. The first seal protrusion portion 27c and the second seal protrusion portion 31d function as a seal portion 80. The seal portion 80 blocks communication between the communication path 40, which passes (through the space) between the outer peripheral surface of the accommodating portion 31 and the inner peripheral surface of the inner plug member 20 (through the discharge hole 22), and the outside (that is, outside the application plug 3 or outside the application container 1, in a state where the overcap 4 is removed from the mouth portion 10), in a state where the overcap 4 is removed from the mouth portion 10 and the plug body 35 closes the communication hole 21. As described above, for example, it is possible to suppress the content liquid remaining in the communication path 40 from leaking out from the space between the outer peripheral surface of the accommodating portion 31 and the inner peripheral surface of the inner plug member 20 (from the discharge hole 22).

As described above, it is possible to provide the application container 1 capable of impregnating the application member 50 with the content liquid before use while suppressing the leakage of the content liquid during use.

In addition, as shown in FIGS. 1 to 3, in a state where the overcap 4 is mounted, the discharge hole 22 is closed, and as shown in FIGS. 4 and 5, when the overcap 4 is removed, the discharge hole 22 is opened, and the holder 30 start to rise, and after that, the communication hole 21 is closed. For this reason, the application container 1 can be brought into a usable state in a state where the internal pressure of the container main body 2 is temporarily released when the overcap 4 is removed. Therefore, it is possible to suppress the leakage of the content liquid during use caused by an increase in the internal pressure of the container main body 2.

In addition, during use, the seal portion 80 can realize blocking of communication between the communication path 40, which passes between the outer peripheral surface of the accommodating portion 31 and the inner peripheral surface of the inner plug member 20, and the outside.

Here, during use, examples of the configuration for blocking communication between the communication path 40, which passes (through the space) between the outer peripheral surface of the accommodating portion 31 and the inner peripheral surface of the inner plug member 20, and the outside, without using the seal portion 80, include a configuration in which the outer peripheral surface of the accommodating portion 31 and the inner peripheral surface of the inner plug member 20 are in sliding contact with each other with lubricant applied therebetween. In this configuration, there is a possibility that the content liquid may be constrained due to the influence of the lubricant.

On the other hand, in the present embodiment, the seal portion 80 can realize blocking of communication between the communication path 40, which passes between the outer peripheral surface of the accommodating portion 31 and the inner peripheral surface of the inner plug member 20, and the outside. Accordingly, the above-described lubricant is unnecessary, and the degree of freedom of the content liquid can be increased.

When the inner plug member 20 or the holder 30 changes with time or the holder 30 vigorously rises, there is a possibility that the plug body 35 excessively bites into the inner plug member 20 due to the biasing force of the biasing member 60.

Here, as shown in FIGS. 4 and 5, the first regulating protrusion portion 27b and the second regulating protrusion portion 31e come into contact with each other in the vertical direction, in a state where the overcap 4 is removed from the mouth portion 10, and the plug body 35 closes the communication hole 21, and the seal portion 80 blocks the communication between the communication path 40 and the outside (in addition, examples of coming into contact between the first regulating protrusion portion 27b and the second regulating protrusion portion 31e in the vertical direction include a form in which the first regulating protrusion portion 27b and the second regulating protrusion portion 31e do not come into contact during general use, but the first regulating protrusion portion 27b and the second regulating protrusion portion 31e come into contact when the plug body 35 is bitten a certain amount into the inner plug member 20). Therefore, as described above, even when the plug body 35 tends to excessively bite into the inner plug member 20 due to the biasing force of the biasing member 60, the first regulating protrusion portion 27b and the second regulating protrusion portion 31e are locked, so that a rise of the holder 30 can be regulated. Accordingly, excessive biting of the plug body 35 into the inner plug member 20 is regulated.

In addition, the technical scope of the present invention is not limited to the above embodiment, and various changes can be made without departing the gist of the present invention.

For example, in the above embodiment, the overcap 4 is in direct contact with the holder 30 to regulate a rise of the holder 30, but the present embodiment is not limited thereto. For example, the overcap may be in contact with the application member to press the application member downward, thereby regulating a rise of the holder.

Additionally, in the above embodiment, the application member 50 protrudes upward from the discharge hole 22 in a state where the overcap 4 is mounted on the mouth portion 10 of the container main body 2, but the present embodiment is not limited thereto. The application member may protrude upward from the discharge hole at least in a state where the overcap is removed.

Further, in the above embodiment, the overcap 4 has a double cylindrical shape, but the present embodiment is not limited thereto. For example, the overcap 4 may be a multi-stage cylindrical shape that expands in diameter in a stepped manner from top to bottom. In this case, for example, the step difference between the upper cylinder portion and the lower cylinder portion may function as the second sealing surface 72a.

In addition, it is possible to appropriately replace the components in the above-described embodiments with well-known components without departing from the scope of the present invention, and the modification examples described above may be combined as appropriate.

INDUSTRIAL APPLICABILITY

According to the present invention, it is possible to provide an application container capable of impregnating an application member with a content liquid before use while suppressing the leakage of the content liquid during use.

REFERENCE SIGNS LIST

1: Application container
2: Container main body
4: Overcap
10: Mouth portion
20: Inner plug member
21: Communication hole
22: Discharge hole
27*b*: First regulating protrusion portion
27*c*: First seal protrusion portion
30: Holder
31: Accommodating portion
31*d*: Second seal protrusion portion
31*e*: Second regulating protrusion portion
35: Plug body
40: Communication path
50: Application member
60: Biasing member
80: Seal portion

The invention claimed is:

1. An application container comprising:

an inner plug member having a cylindrical shape extending in a vertical direction, mounted on a mouth portion of a container main body, and formed with a communication hole which communicates with an inside of the container main body and a discharge hole which communicates with the communication hole and discharges a content liquid of the container main body;

a holder including an accommodating portion that has a bottomed cylindrical shape and is supported movably along the vertical direction inside the inner plug member, and a plug body that opens the communication hole to be closable from below the communication hole in the container main body, and formed with a communication path between the holder and the inner plug member to communicate with an inside of the accommodating portion and an inside of the container main body;

an application member disposed in the accommodating portion and protruding upward from the holder;

a biasing member configured to bias the holder upward with respect to the inner plug member;

an overcap mounted on the mouth portion of the container main body, and configured to close the discharge hole in a state where a rise of the holder is regulated; and a seal portion configured to block communication between the communication path, which passes between an inner peripheral surface of the inner plug member and an outer peripheral surface of the accommodating portion, and an outside, in a state where the overcap is removed from the mouth portion and the plug body closes the communication hole.

2. The application container according to claim 1, wherein the seal portion includes:

a first seal protrusion portion provided on the inner peripheral surface of the inner plug member; and a second seal protrusion portion provided on the outer peripheral surface of the accommodating portion and positioned below the first seal protrusion portion, and a space between the inner peripheral surface of the inner plug member and the outer peripheral surface of the accommodating portion is sealed by the first seal protrusion portion and the second seal protrusion portion coming into contact with each other, in a state where the overcap is removed from the mouth portion and the plug body closes the communication hole.

3. The application container according to claim 1, further comprising:

a first regulating protrusion portion provided on the inner peripheral surface of the inner plug member; and a second regulating protrusion portion provided on the outer peripheral surface of the accommodating portion, wherein the first regulating protrusion portion and the second regulating protrusion portion are configured to come into contact with each other in the vertical direction, in a state where the overcap is removed from the mouth portion, the plug body closes the communication hole, and the seal portion blocks the communication between the communication path and the outside.

4. The application container according to claim 2, further comprising:

a first regulating protrusion portion provided on the inner peripheral surface of the inner plug member; and a second regulating protrusion portion provided on the outer peripheral surface of the accommodating portion, wherein the first regulating protrusion portion and the second regulating protrusion portion are configured to come into contact with each other in the vertical direction, in a state where the overcap is removed from the mouth portion, the plug body closes the communication hole, and the seal portion blocks the communication between the communication path and the outside.

\* \* \* \* \*